US011441112B2

(12) United States Patent
Kaffka et al.

(10) Patent No.: US 11,441,112 B2
(45) Date of Patent: Sep. 13, 2022

(54) INCUBATION DEVICE AND SYSTEM COMPRISING INCUBATION DEVICE AND ROCKING PLATFORM

(71) Applicant: EUROIMMUN Medizinische Labordiagnostika AG, Luebeck (DE)

(72) Inventors: Christian Kaffka, Dassow (DE); Martin Rateike, Pansdorf Schleswig-Holstein (DE); Winfried Stöcker, Gross Groenau (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 665 days.

(21) Appl. No.: 16/429,143

(22) Filed: Jun. 3, 2019

(65) Prior Publication Data
US 2019/0284519 A1   Sep. 19, 2019

Related U.S. Application Data

(63) Continuation of application No. PCT/EP2018/075614, filed on Sep. 21, 2018.

(30) Foreign Application Priority Data

Sep. 22, 2017 (EP) .................... 17192547

(51) Int. Cl.
*C12M 1/00* (2006.01)
*C12M 3/06* (2006.01)
(Continued)

(52) U.S. Cl.
CPC ............ *C12M 27/16* (2013.01); *B01F 31/23* (2022.01); *B01L 9/52* (2013.01); *C12M 41/14* (2013.01);
(Continued)

(58) Field of Classification Search
None
See application file for complete search history.

(56) References Cited

U.S. PATENT DOCUMENTS 8,557,605 B2    10/2013   Stöker et al.
9,488,822 B2 *  11/2016   Machida ................ G01N 1/312
(Continued)

FOREIGN PATENT DOCUMENTS

EP    2 191 893    6/2010
EP    3 085 446    10/2016
(Continued)

OTHER PUBLICATIONS

International Preliminary Report on Patentability dated Apr. 2, 2020 in International Application No. PCT/EP2018/075614, English translation, 7 pages.

(Continued)

*Primary Examiner* — Jyoti Nagpaul
(74) *Attorney, Agent, or Firm* — Grüneberg and Myers PLLC

(57) ABSTRACT

An incubation device has multiple rocking platforms with each platform pivotally mounted about a respective axis. Each rocking platform has a respective receiving device for mechanically reversibly receiving a respective incubation channel. The device also has a common drive unit for common respective rocking movements of each platform from a zero position through with a specific angle range as a result of movement of the drive unit. Each rocking platform is coupled to the drive unit via a respective coupling mechanism, and each coupling mechanism elastically and resiliently couples the respective rocking platform to the drive unit, such that when the rocking platform is restrained, despite continuation of the drive movement, the rocking platform remains motionless in a fixed position. After release of the restraint on the rocking platform, the rocking (Continued)

platform resumes the rocking movement with the specific angle range.

14 Claims, 13 Drawing Sheets

(51) Int. Cl.
    *G01N 1/31*     (2006.01)
    *B01L 9/00*     (2006.01)
    *B01F 31/23*     (2022.01)
    *B01L 3/00*     (2006.01)
    *B01L 1/00*     (2006.01)
    *B01L 7/04*     (2010.01)
    *B01F 101/44*     (2022.01)

(52) U.S. Cl.
    CPC .......... *G01N 1/312* (2013.01); *B01F 2101/44* (2022.01); *B01L 1/00* (2013.01); *B01L 3/50855* (2013.01); *B01L 7/04* (2013.01); *B01L 2300/0822* (2013.01); *B01L 2300/0877* (2013.01); *B01L 2400/049* (2013.01); *B01L 2400/0433* (2013.01); *B01L 2400/0475* (2013.01)

(56) References Cited

U.S. PATENT DOCUMENTS

| | | | |
|---|---|---|---|
| 9,977,040 | B2 | 5/2018 | Stoecker |
| 2010/0124750 | A1 | 5/2010 | Stöker et al. |
| 2014/0186971 | A1 | 7/2014 | Winfried et al. |
| 2018/0078941 | A1 | 3/2018 | Kaffka |

FOREIGN PATENT DOCUMENTS

| | | |
|---|---|---|
| WO | 2014/009067 | 1/2014 |
| WO | 2016/169576 | 10/2016 |

OTHER PUBLICATIONS

English translation of Written Opinion dated Nov. 30, 2018 in PCT/EP2018/075614.
European Search Report dated Feb. 21, 2018 in European Application No. 17192547.2 with English translation.
International Search Report dated Nov. 30, 2018 in PCT/EP2018/075614.
Written Opinion dated Nov. 30, 2018 in PCT/EP2018/075614.
Lemcke et al., "*Automated direct immunofluorescence analyses of skin biopsies,*" J Cutan Pathol 2016; 43: 227-235 DOI: 10.1111/cup.12637.

* cited by examiner

INCUBATION DEVICE AND SYSTEM COMPRISING INCUBATION DEVICE AND ROCKING PLATFORM

CROSS-REFERENCE TO RELATED APPLICATIONS

The present application is a continuation of the International Application PCT/EP2018/075614 filed on Sep. 21, 2018, which in turn claims the benefit of the European Application EP17192547.2 filed on Sep. 22, 2017, all of which are incorporated by reference in their entireties.

BACKGROUND OF THE INVENTION

Field of the Invention

The present invention relates to an incubation device for the pathohistological examination of biological samples, and to a system comprising the incubation device and a rocking platform.

Discussion of the Background

A biological sample is preferably a tissue section, particularly preferably a tissue section of human tissue, a cell section or a protein.

Pathological and laboratory-diagnostic studies constitute an indispensable basis for modem medicine. By now, many tests which can be carried out in a routine fashion are available, with the aid of which crucial information for the present clinical picture, for prognosis or for the outcome of a treatment can be obtained from sample material in the absence of the patient.

In this case, patient samples in the form of tissue sections or cells may initially be dyed, and the dyed structures may then be studied in the course of finding a result. Particularly in the field of histology or histopathology, micrometer-thin dyed tissue sections are produced and evaluated under the microscope.

The sample material for histological work includes above all medical operation preparations, sample excisions and tissue taken by means of biopsies, the main aim in studying tissue sections dyed in this way being reliable detection and typing of tumors. With the aid of such methods, tissues can be histologically characterized and cancer can be diagnosed by studying growths and tumors.

As an alternative, patient samples may be studied for the presence or the concentration of particular molecules, when the values obtained represent useful information for the diagnosis with the reference data. Thus, the detection of specific autoantibodies may indicate that the patient is suffering from an autoimmune disease. Examples of autoimmune diseases include inflammatory diseases such as rheumatoid diseases, metabolic diseases such as diabetes, and neurological diseases.

One unsolved problem is the scarcity and expense of reagents and sample material. Economic considerations are leading to working procedures and material consumption being optimized. In particular, the trend is toward miniaturization: diagnostic, pathohistological and analytical reactions are carried out no longer on the milliliter scale but on the microliter or even nanoliter scale. This saves on reagents and space, and allows a sample once obtained to provide enough starting material for a large number of diagnostic studies. Not least, the patient is spared from retaking of a sample even in the event that an individual diagnostic test fails.

One particular problem with miniaturization is that the ratio of the liquid volume held back by capillary forces and adhesion on surfaces, on the one hand, and the total volume of the liquid used for a method step, on the other hand, is particularly high. In other words, a large amount of liquid adheres on the surfaces to such an extent that it cannot be removed efficiently after a method step by pouring or pipetting.

A relatively large volume of the liquid remains, which interferes with subsequent method steps. For example, a remaining wash solution dilutes a reagent introduced for a subsequent reaction, and thereby reduces the yield or sensitivity of the subsequent reaction.

To this end, European Patent Application EP 3085446 A1 proposed an incubation tray for the incubation of a biological sample, in which a carrier with the biological sample can be placed in order to be able to expose the biological sample in the incubation tray to incubation with one or more liquids.

It is furthermore problematic when individual samples should or must be treated individually, in particular while other samples are being tilted or rocked in the same process. Individual driving and processing of samples is possible only very elaborately or not at all in pathohistological and laboratory-diagnostic studies.

US 2010/0124750 A1 describes a device for carrying out immunological, histochemical and cytochemical, molecular-biological, enzymological, clinical-chemical and other analyses, the device comprising an object carrier having one or more elongate adhesive surfaces and a reagent holder having one or more channels.

WO 2016/169576 A1 describes an incubation tray having an indentation, formed by the walls of the incubation tray, and a bottom, the incubation tray comprising a means for aspiration of liquid at least one longitudinal end of the indentation, preferably an opening which opens into an outlet channel at the longitudinal end of the indentation, particularly preferably in a wall of the incubation tray, the opening and the outlet channel being configured in such a way that a reduced pressure can be applied, the incubation tray being tiltable about its transverse axis, and the incubation tray being able to be equipped with a carrier.

SUMMARY OF THE INVENTION

The object of the invention is to provide a possibility for the pathological or laboratory-diagnostic study of biological samples, so that individual treatment of single samples is made possible while a time saving and an increase in flexibility can be achieved.

This object is achieved by the incubation device according to the invention.

The present invention includes the following embodiments:

1. An incubation device (V),
    comprising a multiplicity of rocking platforms (W), which are respectively mounted tiltably about a respective axis (A), a respective rocking platform (W) comprising a respective reception device (AN) for mechanically reversible reception of a respective incubation tray (I),
    furthermore comprising a common drive unit (AE) for common generation of respective rocking movements of the respective rocking platforms, in particular from a neutral position (NL), through a particular angle range (WB) on the basis of a drive movement of the drive unit (AE), wherein each of the respective rocking platforms (W) is coupled to the drive unit (AE) by means of a respective coupling mechanism (K), and wherein each of the respective coupling mechanisms (K) elastically resiliently couples the respective rocking platform (W) to the drive unit (AE) in such a way that, when the rocking platform (W) is restrained, the rocking platform (W) remains in a fixed position despite continuation of the drive movement, but furthermore, after the restraint of the rocking platform (W) is ended, the rocking platform (W) again carries out the rocking movement through the particular angle range (WB) because of the drive movement.

2. The incubation device according to embodiment 1, wherein the coupling mechanism (K) comprises at least one elastic spring element (F), which is configured in such a way that the spring element (F) is elastically deformed in the event of application of a holding force to restrain the rocking platform (W) and simultaneous continuation of the drive movement.

3. The incubation device according to embodiment 2. wherein the rocking platform (W) comprises a force reception element (KA) arranged eccentrically with respect to the axis (A) of the rocking platform (W), the deflection of which about the axis midpoint (M) causes tilting of the rocking platform (W).

wherein the coupling mechanism (K) furthermore comprises at least one pusher element (MI) which, because of the drive movement of the drive unit (AE), generates a force on the force reception element (KA) to deflect the force reception element (KA), and wherein a force transmission from the pusher element (MI) to the force reception element (KA) is coupled to the spring element (F).

4. The incubation device according to embodiment 1, furthermore comprising a holding device (H) for restraining at least one of the rocking platforms (W) in the fixed position.

5. The incubation device according to embodiment 4, wherein the drive unit (AE) is arranged below the rocking platform (W), wherein the holding device (H) comprises on its lower side an engagement element (EE) having an essentially convex geometrical shape (KOF).

wherein the rocking platform (W) furthermore comprises on its upper side an engagement recess (EM) having an essentially concave geometrical shape (KOF), which corresponds with the convex geometrical shape of the engagement element (EE), and wherein movement of the holding device (H) from above in the direction of the upper side of the rocking platform (W) causes engagement of the engagement element (EE) in the engagement recess (EM) in order to prevent the rocking movement of the rocking platform (W) in the fixed position.

6. The incubation device according to embodiment 2. wherein the rocking platform (W) furthermore comprises a metal element (MT), which is firmly mechanically coupled to the rocking platform (W) and carries out the rocking movement together with the rocking platform (W), wherein the incubation device (V) furthermore comprises an electromagnet (ELM) and a control unit (SE).

wherein the control unit (SE) is configured to drive the holding device (H) in such a way that the holding device (H) restrains the rocking platform (W) in the fixed position, in particular by means of engagement of the engagement element (EE) in the engagement recess (EM), and furthermore subsequently to activate the electromagnet (ELM) so that a magnetic force between the electromagnet (ELM) and the metal element (MT) also restrains the rocking platform (W) in the fixed position when the holding device (H) no longer restrains the rocking platform (W).

7. The incubation device according to embodiment 1, wherein the reception device (AN) is configured with an upwardly open opening (OF) on an upper side of the rocking platform (W), into which the incubation tray (I) can be inserted.

8. The incubation device according to embodiment 7, wherein the reception device (AN) comprises a bottom (B) on which a lower side (U) of the incubation tray (I) bears in the inserted state, and wherein the reception device (AN) furthermore comprises a clamping mechanism (KL1, KL2) in order to hold the lower side (U) of the incubation tray (1) on the bottom (B).

9. The incubation device according to embodiment 8, wherein the rocking platform (W) furthermore comprises a heating device (HZ) for heating the bottom (B).

10. A system, comprising an incubation device (V) according to embodiments 1 to 9 and at least one incubation tray (I) which can be placed in a rocking platform (W)

11. The system according to embodiment 10, wherein the incubation tray (I) comprises an indentation (VT), formed by the walls (WD) of the incubation tray (I), having an indentation bottom (VB), wherein the incubation tray (I) comprises at least one opening (ALO, ELO) which opens into a channel (AKN, EK) at a longitudinal end of the indentation (VT), preferably in a wall (WD) of the incubation tray, so that liquid (FL) can be introduced into the indentation (VT), or aspirated, through the channel (AKN, EL).

wherein a carrier (TR) may be placed in the incubation tray, which carrier comprises the sample (PR) on its lower side (UTR), which faces toward the indentation bottom (VB), when it is placed in the incubation tray, so that the lower side of the carrier (TR), the indentation bottom (VB) and the walls (WD) form a compartment (KAV) or the liquid (FL).

12. The system according to embodiment 11, wherein the incubation tray comprises means (AF) for fixing a distance between the lower side (UT) of the carrier and the indentation bottom (VB) such that the lower side of the carrier, the indentation bottom and the walls form a compartment for the liquid.

DETAILED DESCRIPTION OF THE INVENTION

Figure 1:
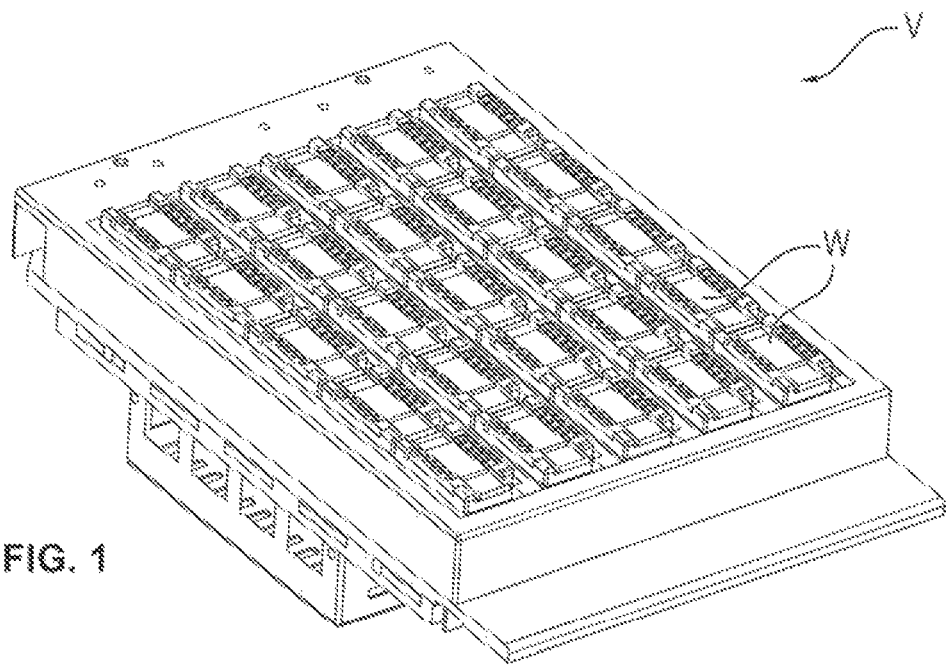
FIG. 1 shows a preferred embodiment of an incubation device.

The invention proposes an incubation device which comprises a multiplicity of rocking platforms, which are respectively mounted tiltably about a respective axis, in particular a longitudinal axis of the rocking platform. A respective rocking platform comprises a respective reception device for mechanically reversible reception of a respective incubation tray. The incubation device furthermore comprises a common drive unit for common generation of respective common rocking movements of the respective rocking platforms from a neutral position through a particular angle range on the basis of a drive movement of the drive unit. Each of the respective rocking platforms is coupled to the drive unit by means of a respective coupling mechanism. Each of the respective coupling mechanisms elastically resiliently couples the respective rocking platform to the drive unit in such a way that, when the rocking platform is restrained, the rocking platform remains in a fixed position despite continuation of the drive movement, but furthermore, after the restraint of the rocking platform is ended, the rocking platform again carries out the rocking movement through the predetermined angle range because of the drive movement.

In particular, one mechanical coupling of a particular rocking platform to the drive unit by means of a particular coupling mechanism is independent of another mechanical coupling of another rocking platform to the drive unit by means of another coupling mechanism.

Also proposed is a system comprising an incubation device according to the invention, and at least one incubation tray which can be placed in a rocking platform.

The incubation tray comprises in particular an indentation, formed by the walls of the incubation tray, having an indentation bottom, the incubation tray furthermore comprising in particular at least one opening which opens into a channel at a longitudinal end of the indentation, preferably in a wall of the incubation tray, so that liquid can be introduced into the indentation, or aspirated, through the channel. In particular a carrier may be placed in the incubation tray, which carrier comprises the sample on its lower side, which faces toward the indentation bottom, when it is placed in the incubation tray, so that the lower side of the carrier, the indentation bottom and the walls form a compartment for the liquid. Preferably, the incubation tray comprises means for fixing a distance between the lower side of the carrier and the indentation bottom, so that the lower side of the carrier, the indentation bottom and the walls form a compartment for the liquid.

In order to explain one or more advantages which may possibly be achieved by the invention, further comments now follow.

In the course of pathohistological studies, in laboratory operation it is often the case that a carrier having a biological sample or a biological tissue must at a first instant be placed in a first incubation tray in order then, in the course of a so-called wash protocol, to bring the tissue successively in contact with different wash liquids in a plurality of wash steps. Sometimes, incubation trays are used into which an object carrier with the sample on the lower side of the object carrier is placed from above, in such a way that the sample lies opposite a bottom of the incubation tray. Preferably, in this case a distance between the sample and the bottom is maintained by spacer elements, so that a cavity is formed between the sample and the bottom by this distance, inside which a liquid is intended to be located. In this case, it may happen that there are air inclusions below the sample, i.e. between the sample and the bottom of the incubation tray. By tilting of the rocking platform, a movement of the liquid is then induced, so that such air inclusions move to the sides of the incubation tray and can emerge there at corresponding openings of the incubation tray. In this way as well, a uniform distribution of liquid on the sample can be ensured. In order to be able to ensure a uniform distribution of a wash liquid on the tissue, a rocking platform is mounted tiltably so that the liquid can move to and fro in the incubation tray during the rocking movement. Since carrying out a full wash protocol with a plurality of wash steps takes a certain length of time, it may happen that the need arises to process another biological sample with another wash protocol, and other associated wash steps, while a first wash protocol for a first biological sample is still being carried out. To this end, this further biological sample thus then needs to be placed in a further incubation tray at a later instant, possibly while the first wash protocol for the first sample is still being carried out.

An incubation tray in this case preferably comprises an opening for introduction of wash liquids as well as an opening for aspiration of wash liquids of the individual wash steps. An incubation tray which has been used once for a particular wash protocol, or a sequence of wash steps, should for reasons of cross-effects or contamination not be used immediately for another biological sample. It is therefore necessary that an incubation tray can be placed in a rocking platform and also taken out again therefrom. This is made possible by the mechanically reversible reception in the reception device of the incubation device according to the invention. If different wash protocols are then possibly intended to be carried out at different instants for different biological samples, in laboratory operation the need may arise to insert different incubation trays in different rocking platforms, and possibly also take them out again, at different times.

If a single rocking platform having its own respective drive unit were respectively to be provided for each individual incubation tray, a separate incubation device with its own drive unit and its own rocking platform would need to be provided for each biological sample. Yet because the incubation device according to the invention comprises a multiplicity of rocking platforms, which are subjected by a common drive unit to a common, in particular common synchronous, rocking movement, the incubation device according to the invention can be used for the processing or execution of wash steps of respective wash protocols for respective biological samples. To this end, for a particular biological sample, it is then merely necessary to place a corresponding incubation tray in a corresponding reception device of a corresponding rocking platform respectively.

For cost reasons, provision may be made that a common drive unit causes the rocking movements of the respective rocking platforms, although for the steps of inserting an incubation tray into a reception device of the rocking platform or the extraction of an incubation tray from a reception device of a rocking platform by a laboratory worker, a great deal of manual dexterity needs to be applied in order to be able to put in or remove the incubation tray during a continuing rocking movement of a rocking platform. As an alternative, the drive unit may be stopped for all rocking platforms in order to put in or remove an individual incubation tray without interference. In this way, particular wash steps for particular samples of particular incubation trays, or rocking platforms, would no longer be carried out continuously, and therefore a processing result would possibly be vitiated. Furthermore, for proper conduct of wash protocols and the corresponding wash steps, it is necessary to remove, or withdraw, from an incubation tray the wash liquid contained therein at different successive instants, for example by aspiration, and then to introduce or pipette a next, different wash liquid into the incubation tray for a next wash step. For this as well, a laboratory worker would need to apply a great deal of manual dexterity when wishing to use manually operated instruments for these tasks during a continuing rocking movement of the rocking platforms. Yet because according to the invention a coupling mechanism is provided for each rocking platform, which elastically resiliently couples the respective rocking platform to the drive unit so that when the rocking platform is restrained, the rocking platform remains in a fixed position despite continuation of the drive movement, but furthermore, after the restraint of the rocking platform is ended, the rocking platform again carries out the rocking movement through the particular angle range because of the drive movement, it is advantageously possible to avoid stopping the drive unit and therefore stopping all of the rocking platforms. A particular rocking platform can be straightforwardly restrained, either by a laboratory worker or else by a holding device of an automated machine, without needing to interrupt the drive movement for inducing the movement of the other rocking platforms. During the restraint of the rocking platform, an incubation tray may then for example be put in or taken out. It is then, however, also possible during the restraint to aspirate liquids from an incubation tray, or pipette them into one. The incubation device according to the invention is therefore particularly advantageous since it allows processing of a multiplicity of biological samples on a multiplicity of rocking platforms, or corresponding incubation trays, the respective wash procedures of the respective biological samples on the respective rocking platform not having to be started at the same instants, but rather they may begin and end at different instants. It is thus not necessary to interrupt a wash process of another rocking platform, or of another biological sample in another incubation tray, when only one particular rocking platform or one particular biological sample is affected. This leads to an increase in flexibility as well as to a time saving in the course of processing a plurality of biological samples by respective wash steps. In particular, samples may be introduced into the overall process, or removed from the overall process, at different times.

By the elastically resilient coupling between the drive unit and the rocking platform, it is furthermore possible to ensure that, for a laboratory worker during manual intervention on or in a rocking platform, a risk of jamming his finger between the rocking platform and, for example, a further rocking platform or other components is avoided since the rocking platform is not rigidly coupled to the drive unit. In this way, higher occupational safety for laboratory workers can be ensured.

A possibility is thus provided of allowing individual treatment of individual biological samples. Advantageously, individual treatment of individual biological samples is possible, in particular while other biological samples are being tilted on other rocking platforms in corresponding incubation trays. It is thus advantageous that a multiplicity of such incubation trays, or rocking platforms, can be used simultaneously and that they can be driven individually.

Advantageous embodiments of the invention are the subject-matter of the dependent embodiments and will be explained in more detail in the description below, sometimes with reference to the figures.

Preferably, the coupling mechanism comprises at least one elastic spring element, which is configured in such a way that the spring element is elastically deformed in the event of application of a holding force to restrain the rocking platform and simultaneous continuation of the drive movement.

The rocking platform preferably comprises a force reception element arranged eccentrically with respect to the axis of the rocking platform, the deflection of which about the axis midpoint causes tilting of the rocking platform, the coupling mechanism furthermore comprising at least one pusher element which, because of the drive movement of the drive unit, generates a force on the force reception element to deflect the force reception element, and a force transmission from the pusher element to the force reception element being coupled to the spring element.

The incubation device furthermore preferably comprises a holding device for restraining at least one of the rocking platforms in the fixed position.

The drive unit is preferably arranged below the rocking platform, the holding device preferably comprising on its lower side an engagement element having an essentially convex geometrical shape, the rocking platform furthermore preferably comprising on its upper side an engagement recess having an essentially concave geometrical shape, which corresponds with the convex geometrical shape of the engagement element, and movement of the holding device from above in the direction of the upper side of the rocking platform preferably causing the rocking platform to bring about engagement of the engagement element in the engagement recess in order to prevent the rocking movement of the rocking platform in the fixed position.

The rocking platform furthermore preferably comprises a metal element, which is firmly mechanically coupled to the rocking platform and carries out the rocking movement together with the rocking platform, the incubation device furthermore preferably comprising an electromagnet and a control unit, the control unit being configured to drive the holding device in such a way that the holding device restrains the rocking platform in the fixed position, in particular by means of engagement of the engagement element in the engagement recess, and furthermore subsequently to activate the electromagnet so that a magnetic force between the electromagnet and the metal element also restrains the rocking platform in the fixed position when the holding device no longer restrains the rocking platform.

Preferably, the reception device is preferably configured with an upwardly open opening on an upper side of the rocking platform, into which the incubation tray can be inserted.

The reception device preferably comprises a bottom on which a lower side of the incubation tray bears in the inserted state, and the reception device preferably furthermore comprising a clamping mechanism in order to hold the lower side of the incubation tray on the bottom.

Preferably, the rocking platform furthermore comprises a heating device for heating the bottom.

Figure 2:
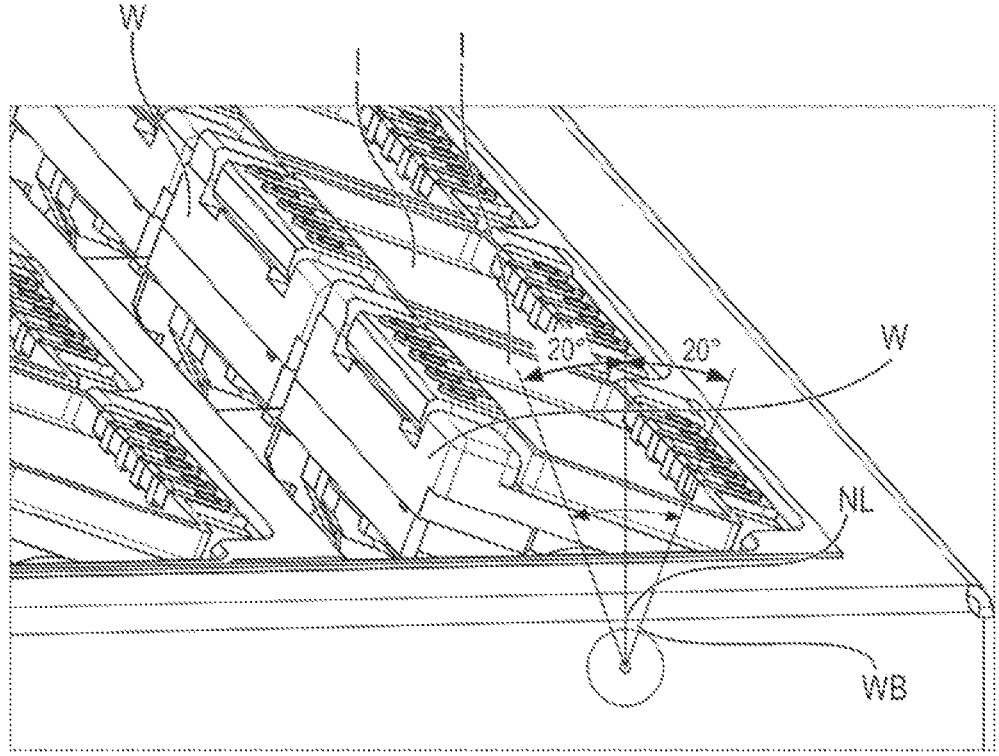
FIG. 2 shows preferred embodiments of rocking platforms.

The invention % ill be explained in more detail below with the aid of particular embodiments, without restriction of the general inventive concept, with the aid of the figures in which:

FIG. 1 shows a preferred embodiment of an incubation device,

FIG. 2 shows preferred embodiments of rocking platforms,

FIGS. 3A to 3D show details of a preferred embodiment of a rocking platform.

Figure 4A:
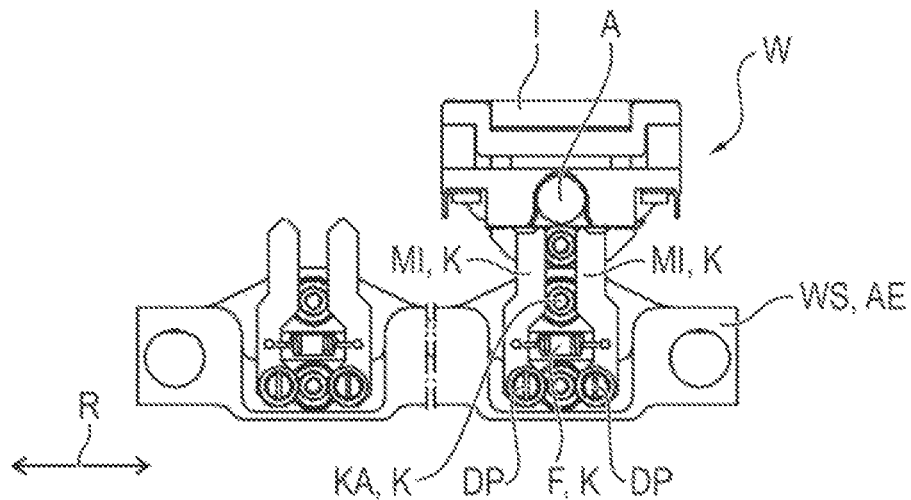
FIGS. 4A to 4C show an interaction of a drive unit with a rocking platform by means of a coupling mechanism according to a preferred embodiment.
Figure 4B:
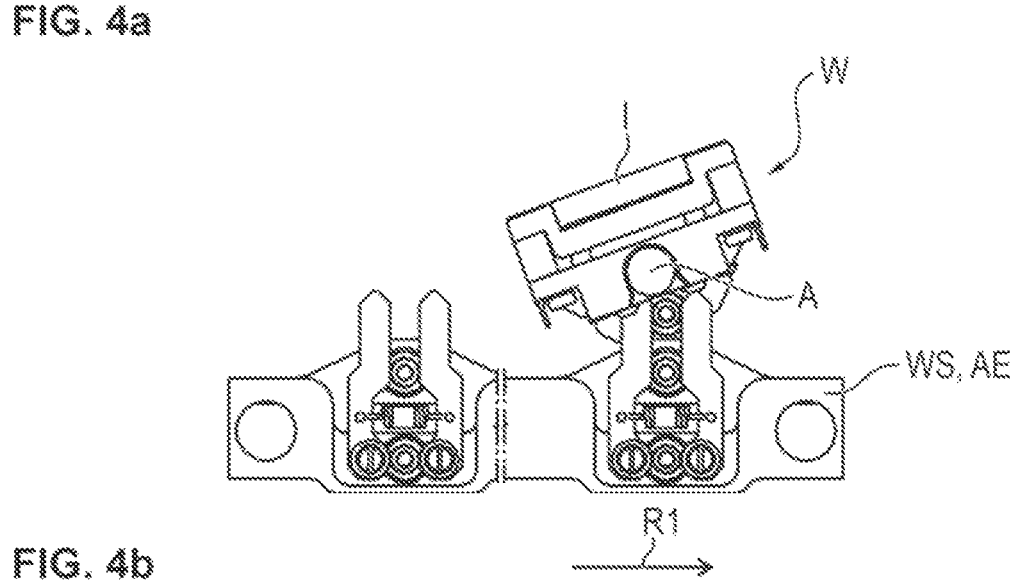
Figure 4C:
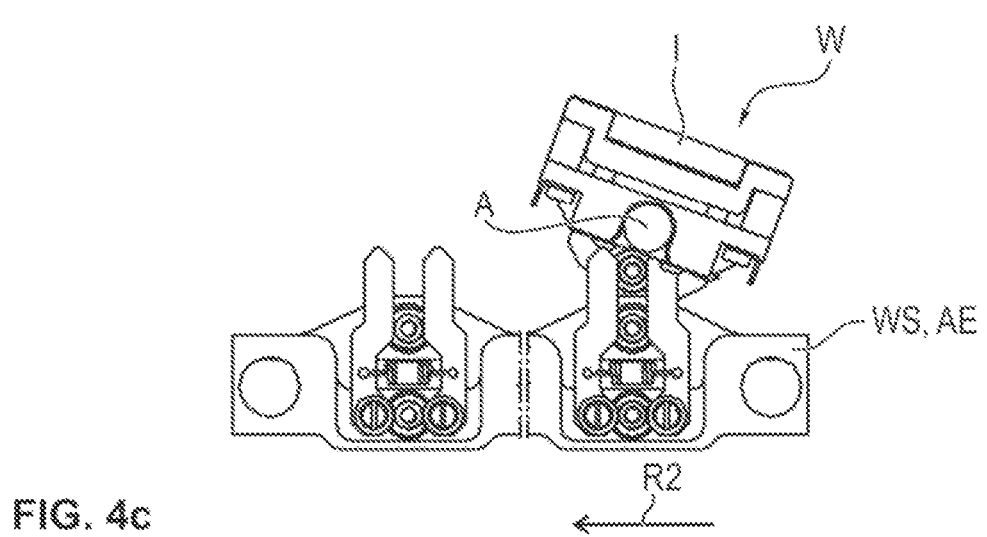
Figure 5:
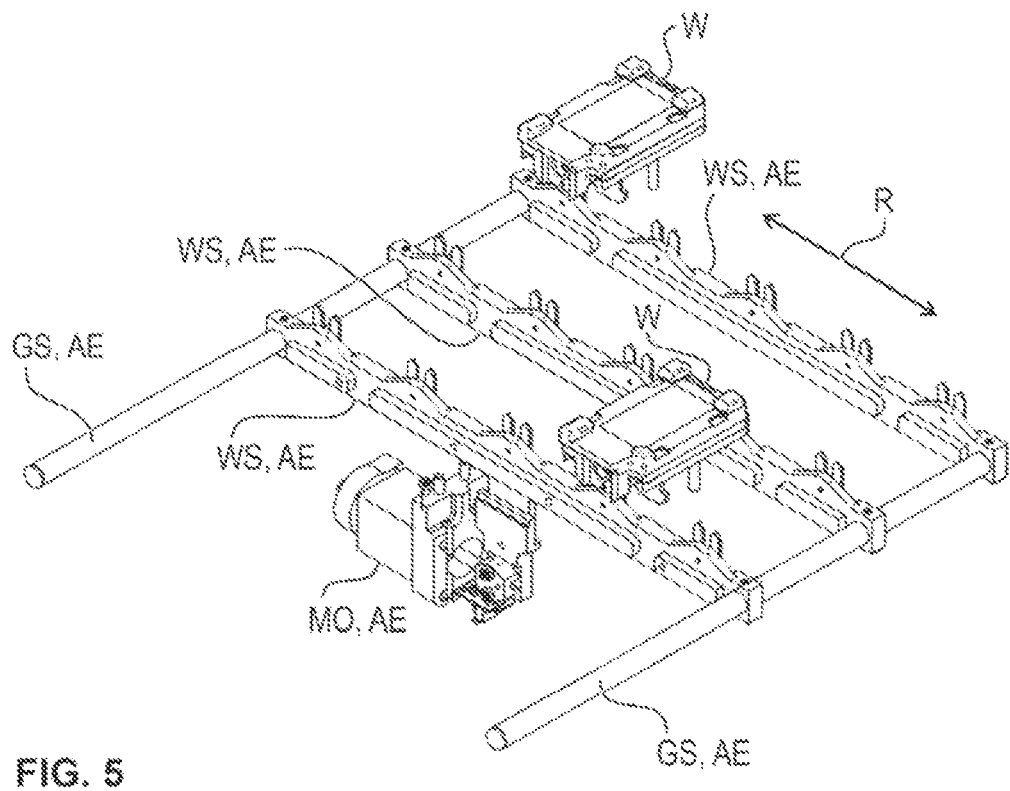
FIG. 5 shows a preferred embodiment of a drive unit.
Figure 6:
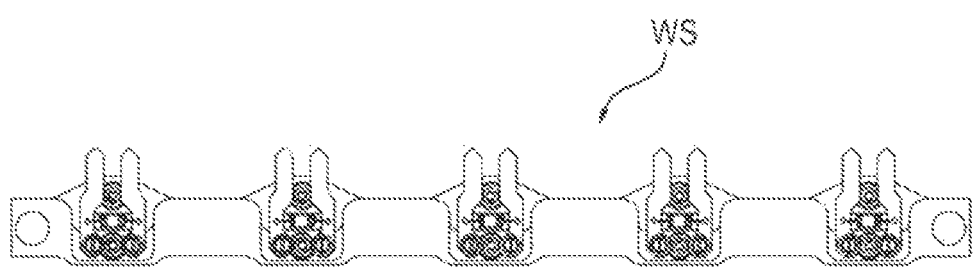
FIG. 6 shows a sub-element of a preferred embodiment of a drive unit.
Figure 7A:
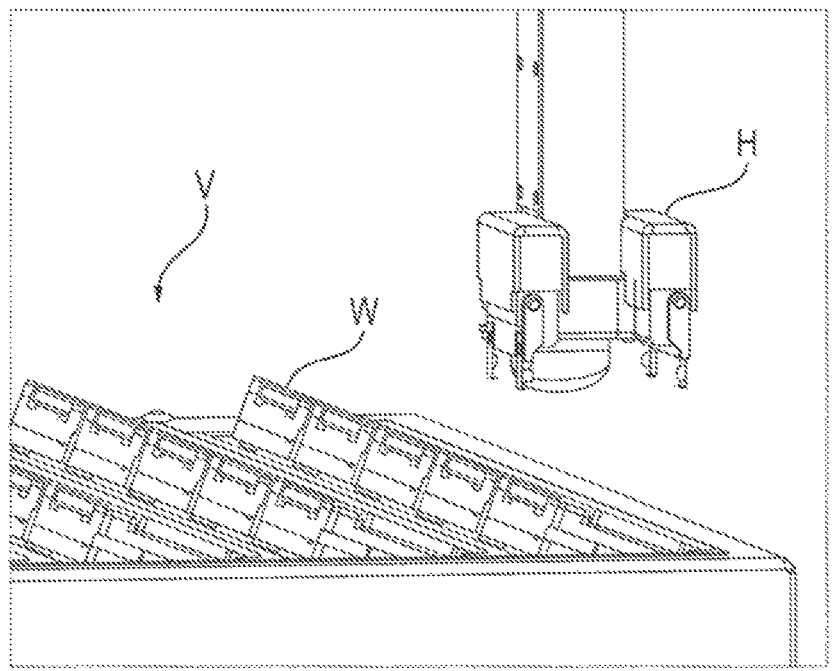
FIGS. 7A and 7B show a use of a holding device.
Figure 7B:
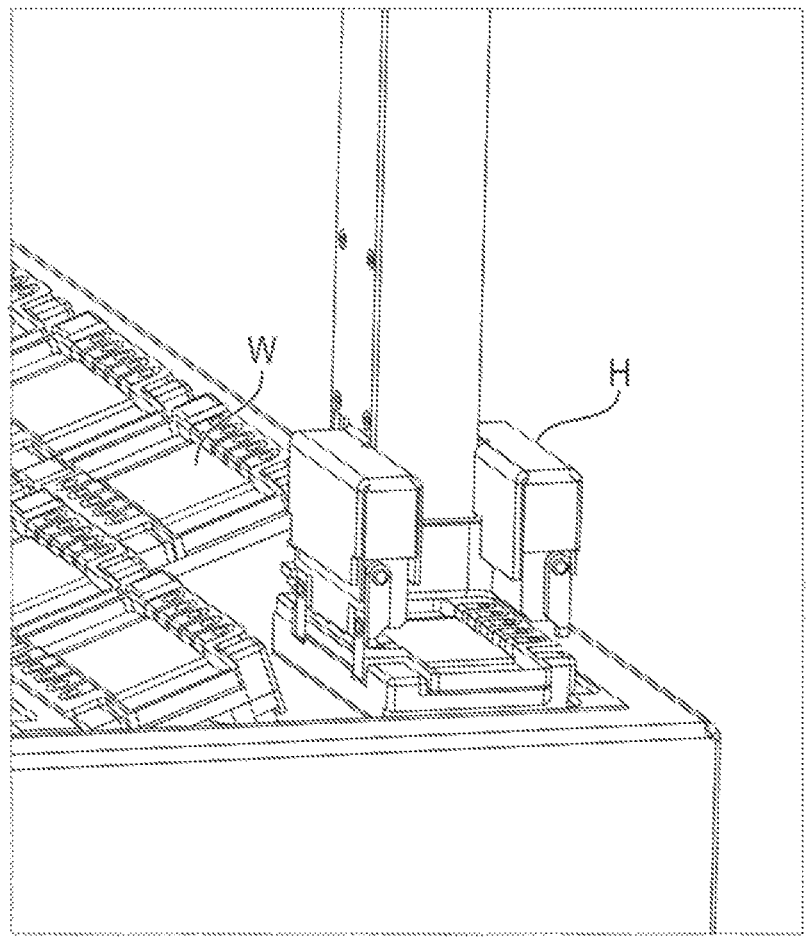
Figure 8A:
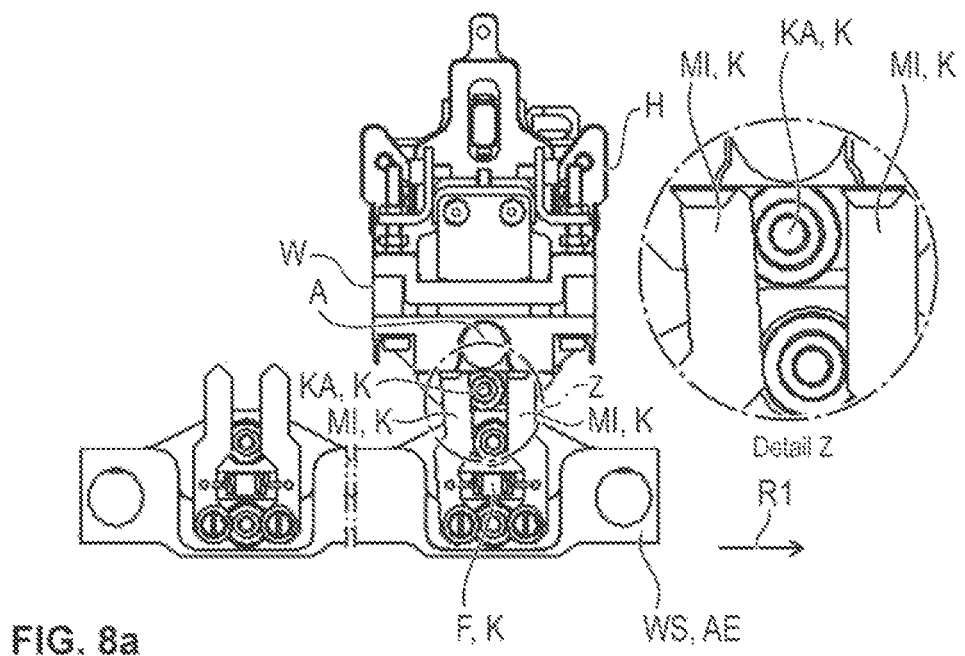
FIGS. 8A and 8B show fixing of a position of a rocking platform by a holding device.
Figure 8B:
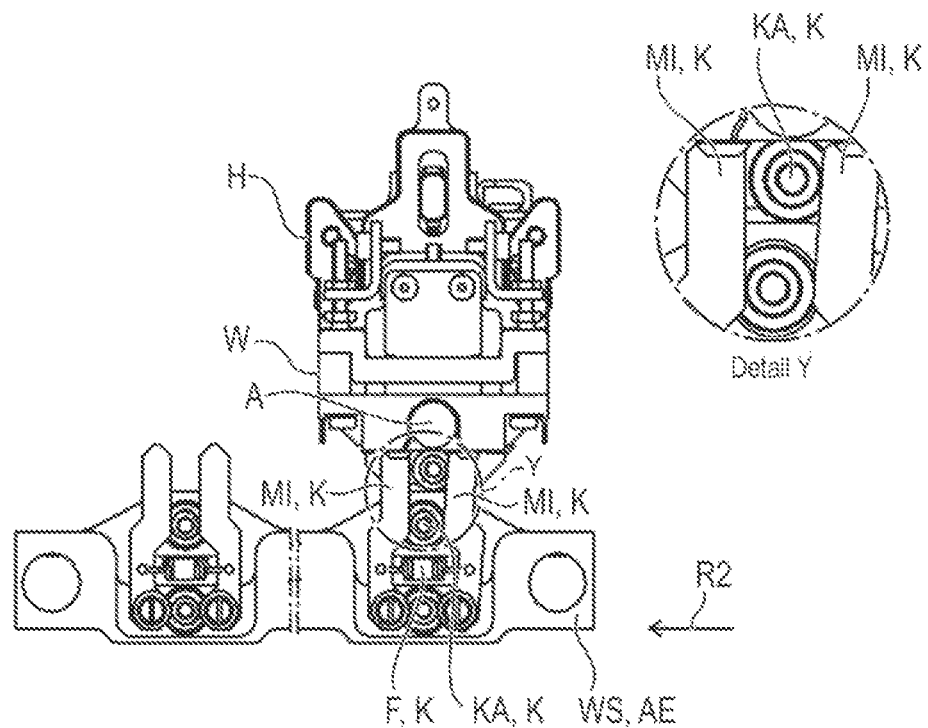
Figure 9A:
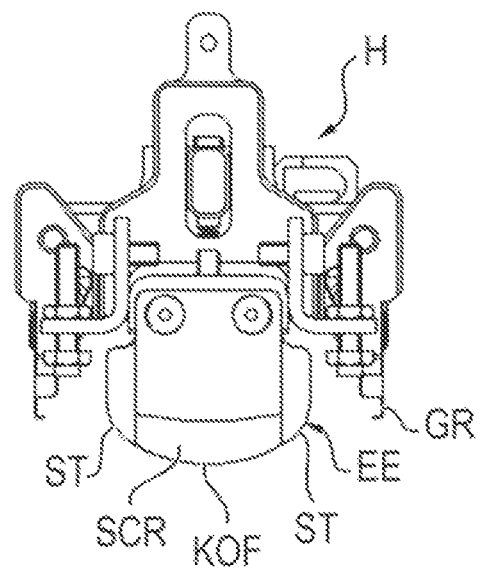
FIGS. 9A and 9B show a preferred embodiment of a holding device.
Figure 9B:
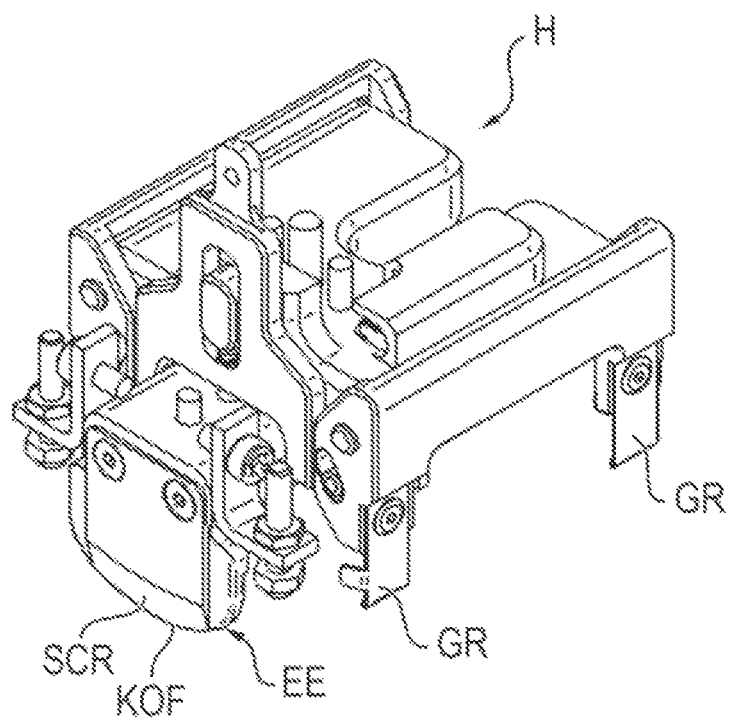
Figure 10A:
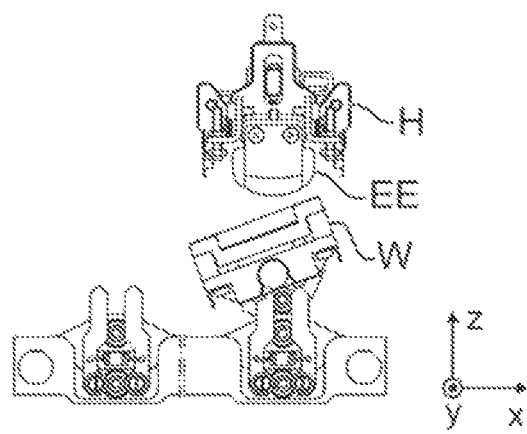
FIGS. 10A to 10D show different positions of a holding device and of a rocking platform during use of a holding device.
Figure 10B:
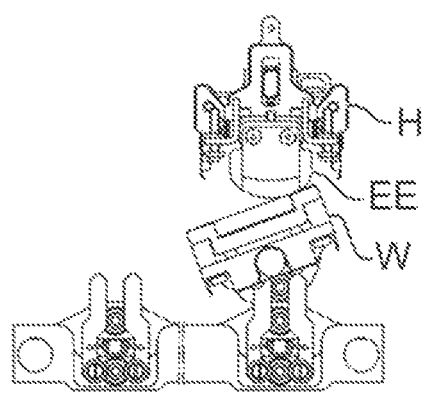
Figure 10C:
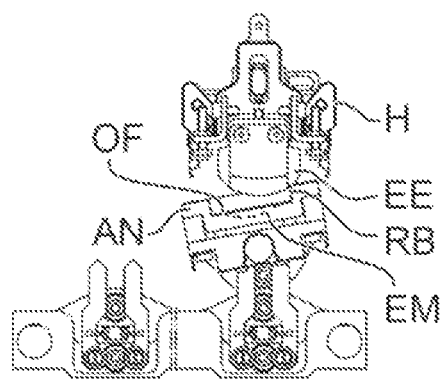
Figure 10D:
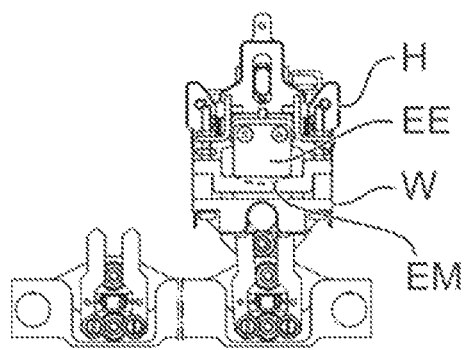
Figure 11A:
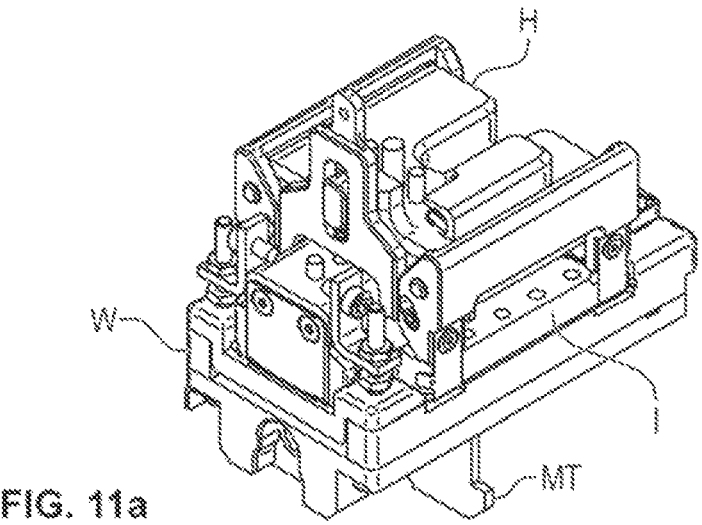
FIGS. 11A to 11C show a preferred embodiment of a reception device.
Figure 11B:
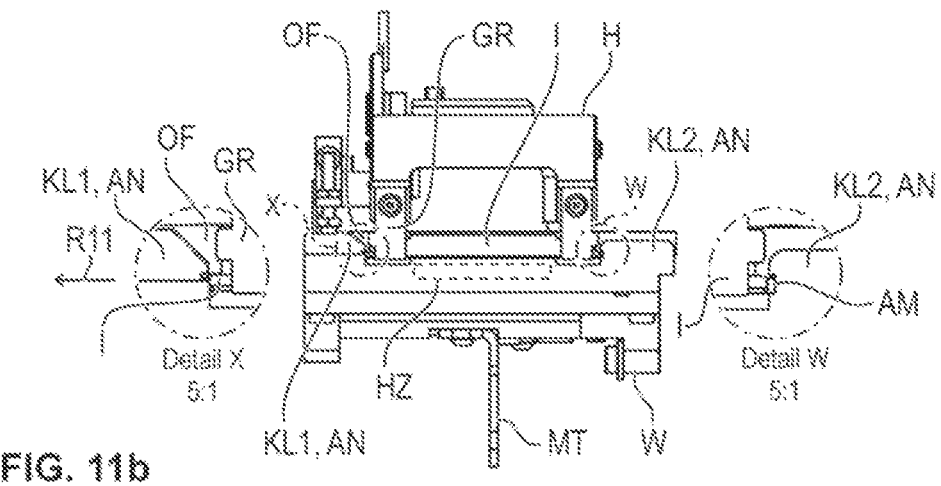
Figure 11C:
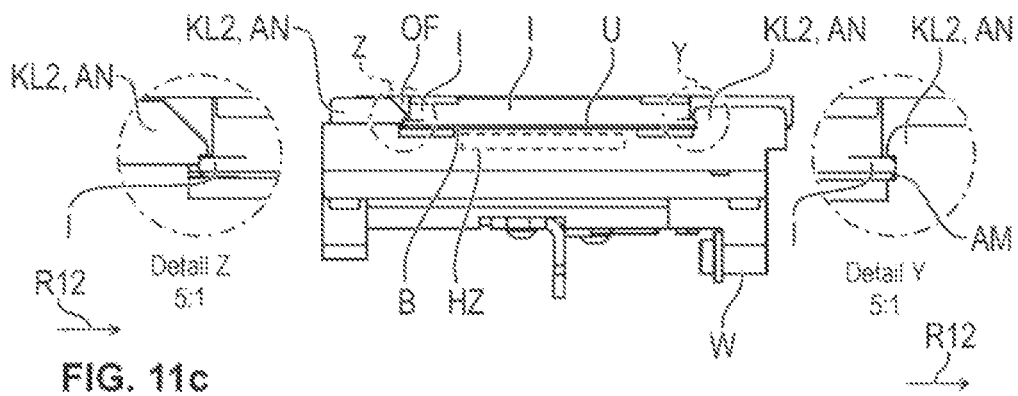
Figure 12A:
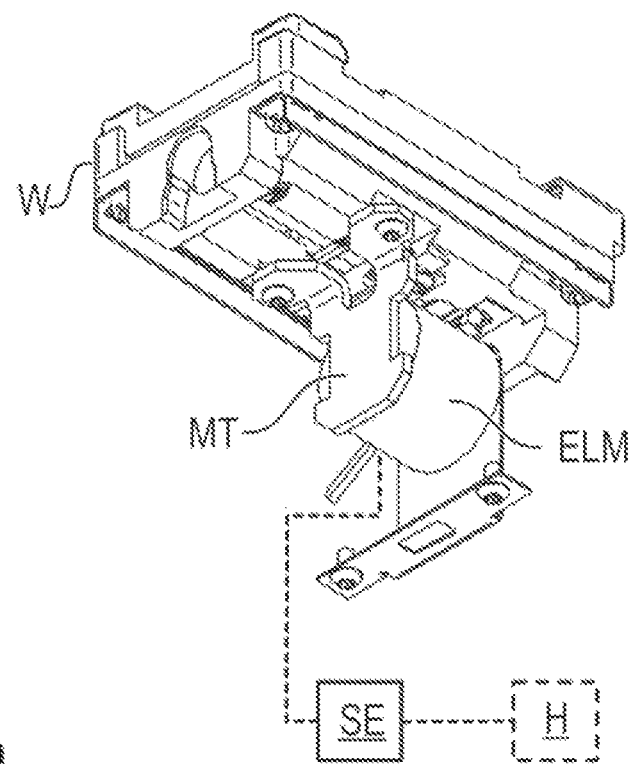
FIGS. 12A and 12B show a preferred embodiment of a rocking platform having a metal element with use of an electromagnet.
Figure 12B:
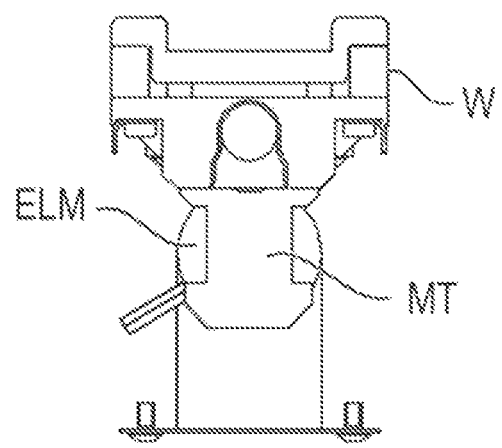
Figure 13A:
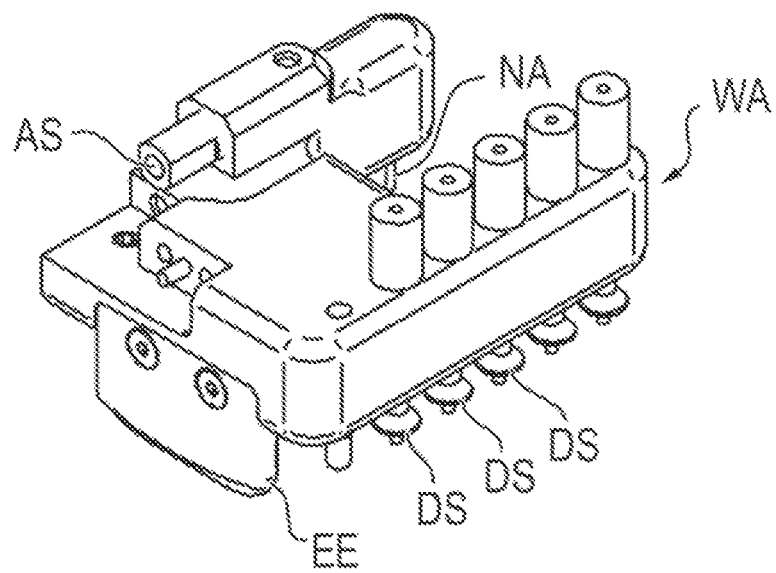
FIGS. 13A and 13B show preferred embodiments of a washing unit.
Figure 13B:
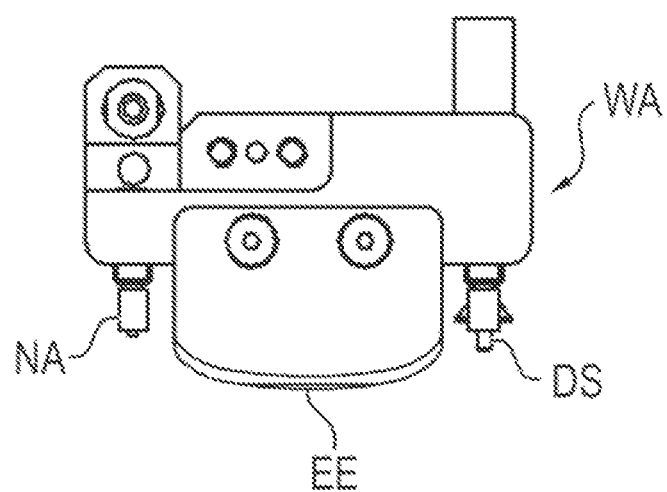
Figure 14:
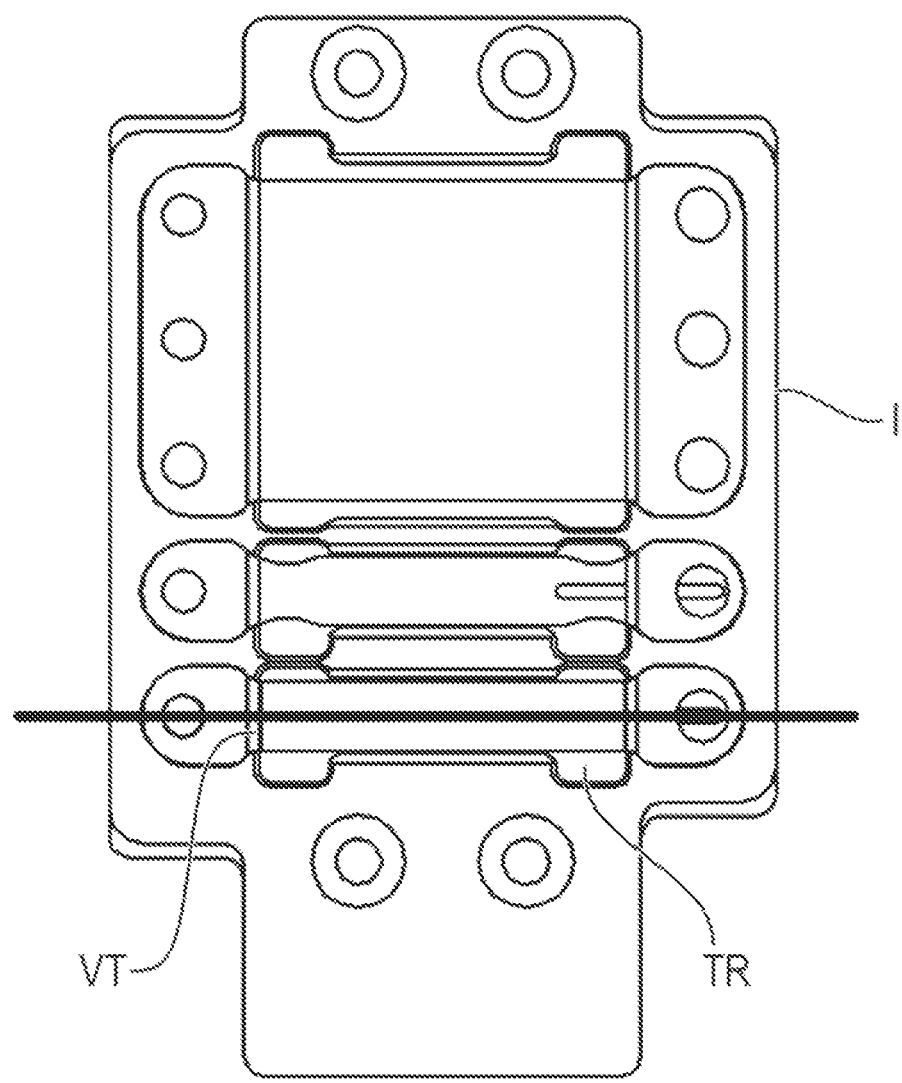
FIG. 14 shows a preferred embodiment of an incubation tray in a plan view.
Figure 15:
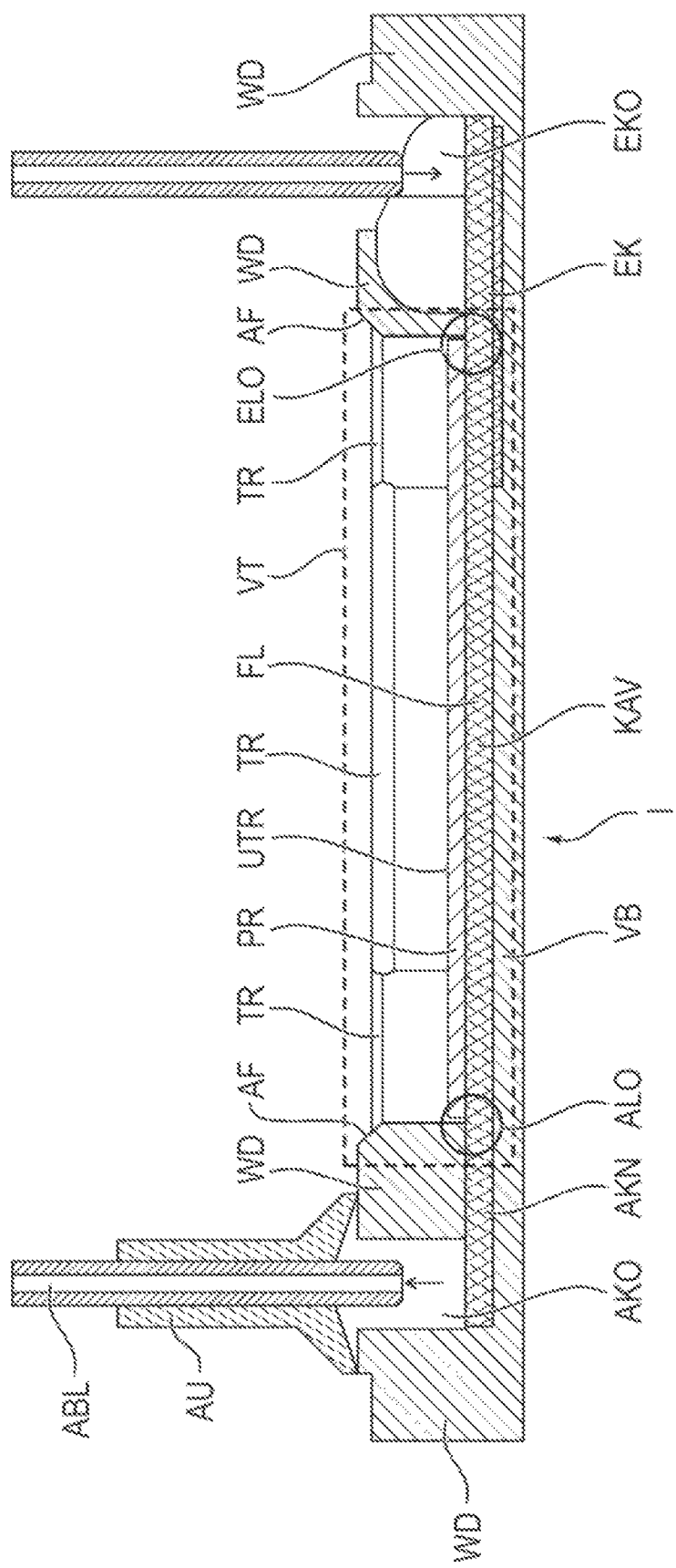
FIG. 15 shows a preferred embodiment of an incubation tray in a sectional view.

FIGS. 4A to 4C show an interaction of a drive unit with a rocking platform by means of a coupling mechanism according to a preferred embodiment, FIG. 5 shows a preferred embodiment of a drive unit, FIG. 6 shows a sub-element of a preferred embodiment of a drive unit, FIGS. 7A and 7B show a use of a holding device, FIGS. 8A and 8B show fixing of a position of a rocking platform by a holding device, FIGS. 9A and 9B show a preferred embodiment of a holding device, FIGS. 10A to 10D show different positions of a holding device and of a rocking platform during use of a holding device, FIGS. 11A to 11C show a preferred embodiment of a reception device, FIGS. 12A and 12B show a preferred embodiment of a rocking platform having a metal element with use of an electromagnet, FIGS. 13A and 13B show preferred embodiments of a washing unit, FIG. 14 shows a preferred embodiment of an incubation tray in a plan view, FIG. 15 shows a preferred embodiment of an incubation tray in a sectional view. FIG. 1 shows an incubation device V having a plurality of rocking platforms W. A deflection, or a tilt, of the rocking platforms W through an angle range WB about a neutral position NL is shown in FIG. 2. Preferably, the angle range is plus/minus 20°. The rocking platforms W are mounted tiltably about respective axes. Respective incubation trays I are placed in the rocking platforms W. The incubation trays are preferably configured as described in European Patent Application EP 3 085 446 A1.

Preferably, the predetermined angle range comprises a range of from −35° to +35°, preferably a range of from −25° to +25°, particularly preferably a range of from −20° to +20°, about the neutral position. The angle range of from −25° to +25° advantageously favors incubation. The angle ranges of from −25° to +25° and from −35° to +35° advantageously favor liquid replacement in the incubation tray with the use of the force of gravity. Aspiration is furthermore favored without incubation regions in the incubation tray becoming dry in a maximum rocking position. In other preferred embodiments, the predetermined angle range comprises a range of from −90° to +90°) about the neutral position. The predetermined angle range allows adjustment of the rocking angle, preferably adaptation of the rocking angle to the viscosity of the liquid, in order on the one hand to achieve an optimal liquid distribution during the incubation and, on the other hand, to prevent incubation regions in the incubation tray becoming dry in a maximum rocking position. By adjustment of the rocking angle, liquid flowing out or overtilting of the incubation tray is preferably avoided.

FIG. 14 shows an incubation tray I in a preferred embodiment from above. Preferably, the incubation tray comprises a multiplicity of incubation sub-trays TR with a respective indentation V. The black bar marks the position at which the cross section of the incubation tray I as represented in FIG. 15 lies.

FIG. 15 shows the incubation tray in cross section at the position marked with the black bar in FIG. 14. The incubation tray comprises respective walls WD on its respective longitudinal sides. On one side of the incubation tray, there is an outlet compartment AKO which is connected to the indentation VT, which can be filled with a liquid FL, represented by dashes in FIG. 15, by means of an outlet channel AKN. A carrier TR placed in the incubation tray I comprises a biological sample PR on its lower side. When enough liquid FL is introduced, the sample PR is immersed, or at least partially covered, in the liquid FL. By application of reduced pressure, liquid FL can be aspirated from an outlet compartment AKO by means of a discharge line ABL located in a separate aspiration hood AU. The liquid FL can be introduced into an inlet compartment EKO through an inlet channel EK. The inlet channel EK and outlet channel AKN open into the indentation in the form of an inlet compartment opening ELO, respectively outlet compartment opening ALO. In FIG. 15, the bottom of the inlet compartment ELO preferably lies below the plane of the bottom of the indentation.

The incubation tray I therefore comprises in particular an indentation VT, formed by the walls WD of the incubation tray I, having an indentation bottom VB, the incubation tray I furthermore comprising in particular at least one opening ELO, ALO which opens into a channel EK, AKN at a longitudinal end of the indentation, preferably in a wall WD of the incubation tray I, so that liquid FL can be introduced into the indentation VT, or aspirated, through the channel EK, AKN. In particular, a carrier TR may be placed in the incubation tray I, which carrier comprises the sample on its lower side UTR, which faces toward the indentation bottom VB, when placed in the incubation tray I, so that the lower side UTR of the carrier TR, the indentation bottom VB and the walls WD form a compartment or a cavity KAV for the liquid FL. Preferably, the incubation tray I has means AF for fixing a distance between the lower side UTR of the carrier TR and the indentation bottom VB, so that the lower side UTR of the carrier TR, the indentation bottom VB and the walls WD form a compartment or a cavity KAV to the liquid FL. These means are, for example, provided in the form of bearing chamfers AF on which the carrier TR can be placed in one or more edge regions of the indentation.

In other preferred exemplary embodiments, the biological sample comprises a sample selected from a group consisting of tissue, preferably tissue sections or tissue biopsies, for example frozen sections, biological cells such as eukaryotic or prokaryotic cells or products thereof, viruses, purified, isolated or artificially produced molecules such as nucleic acids, polypeptides, lipids or carbohydrates. Preferably, a biological sample is of human or animal origin.

In one preferred exemplary embodiment of the invention, the incubation tray comprises an outlet channel, having an outlet channel opening, for removing liquid from the incubation tray by means of aspiration, which channel is configured in such a way that the carrier is not removed or damaged during the aspiration. In another preferred exemplary embodiment, it is a tube whose end is inserted into the liquid. Preferably, it is a channel integrated into the incubation tray. Pressure may be applied to the outlet channel for the aspiration.

The width of the outlet channel is preferably from 50% to 100%, particularly preferably from 60% to 95%, more particularly preferably from 75% to 95% of the width of the indentation of the incubation tray or of the carrier, preferably of the carrier.

The opening of the outlet channel is arranged vertically starting from the plane of the bottom, in such a way that at least a part of it, preferably the entire opening, lies below the surface of a liquid with which the incubation tray is filled, preferably filled to such an extent that the carrier is just fully covered with liquid. Preferably, the opening is arranged on the bottom. This is the case when liquid contained in the incubation tray, apart from residues that adhere on surfaces, can flow away fully when the incubation tray is inclined in such a way that the liquid flows in the direction of the opening.

In another preferred exemplary embodiment, the outlet channel is under a reduced pressure, which is preferably dimensioned at least in such a way that liquid is aspirated in the indentation. The delivery rate with which the liquid is aspirated may be from 0.1 to 10 l/min, preferably from 0.2 to 5 l/min, particularly preferably from 0.3 to 3 l/min. Conventional aspiration devices may be used, for example diaphragm, gear, piston or peristaltic pumps. The aspiration of the liquid may be carried out continuously or discontinuously. In this preferred exemplary embodiment, the aspiration is carried out continuously. i.e. the majority of the liquid is not aspirated at once, for example at the end of the incubation process, but in a plurality of steps. Preferably, in a method step which comprises the incubation of the carrier in a liquid, at least one instant, preferably for a duration of at least 10, 20, 30, 60, 120, 300, 600 seconds, 10, 15, 20 or 30 minutes, liquid is simultaneously introduced at one end of the incubation tray and aspirated at the other end of the incubation tray. In this way, the carrier only ever comes in contact with unused fresh liquid. This accelerates the processing of the carrier, or of the biological sample. In other preferred exemplary embodiments, after introduction of the liquid, the carrier is initially incubated therein, preferably for a duration of at least 10, 20, 30, 60, 120, 300 seconds, 10, 15 or 30 minutes, before the liquid is aspirated.

The incubation tray may be filled with a liquid, preferably an aqueous liquid, particularly preferably a wash buffer or reagent for processing a sample on the carrier. The volume of the liquid is dimensioned in such a way that the biological sample is in sufficient contact therewith. In one preferred exemplary embodiment, the volume of the liquid in the incubation tray is dimensioned in such a way that it fully covers the carrier and the sample thereon in the horizontal position. In other preferred exemplary embodiments, it is dimensioned in such a way that the liquid fully covers a sample which is arranged on the side of the carrier that faces toward the bottom. As an alternative, it is dimensioned in such a way that it fully wets the sample not continuously but periodically when the incubation tray is tilted or rocked during the incubation. While in the case of readily available solutions such as nonspecific wash buffers, for example PBS, or solutions for developing a signal, an excess may be used, in the case of other solutions such as reagents which are difficult to obtain and are available only in small volumes, for example antibodies, in particular primary antibodies, the user is restricted to the minimum volume absolutely necessary.

Optionally, the incubation tray comprises an inlet channel. This is a closed means for the supply of liquid, which need not be configured pressure-tightly. The delivery may take place directly into the incubation tray.

The incubation module, or the multiplicity of incubation trays or the multiplicity of rocking platforms, may preferably be moved in such a way that the liquid is thoroughly mixed and its exposure to the respective carrier is promoted, for example by tilting or rocking, vibration, shaking or the like. In preferred exemplary embodiments, the incubation tray can be tilted about the axis so that the liquid moves in the direction of the lower-lying longitudinal end of the incubation tray. In the tilted state, particularly when the outlet opening is located at the longitudinal end and the outlet channel opening is located at its bottom, removal of the liquid is particularly simple and efficient. During the tilting, the incubation tray preferably makes an angle of from 1° to 45° with the base surface, particularly preferably from 2.5° to 30°, even more preferably from 7.5° to 25°.

Figure 3C:
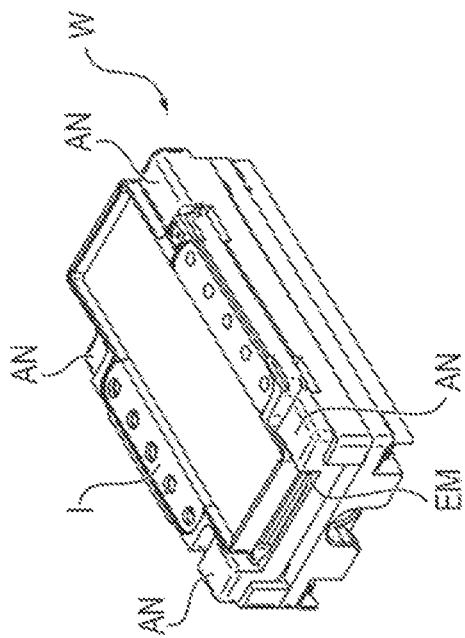
FIGS. 3A to 3D show details of a preferred embodiment of a rocking platform.
Figure 3D:
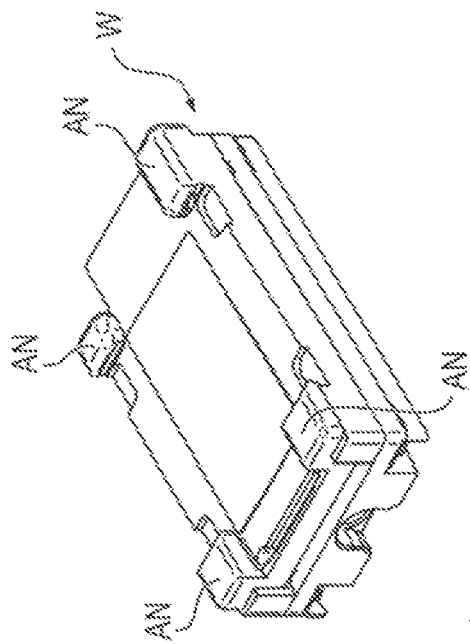
Figure 3A:
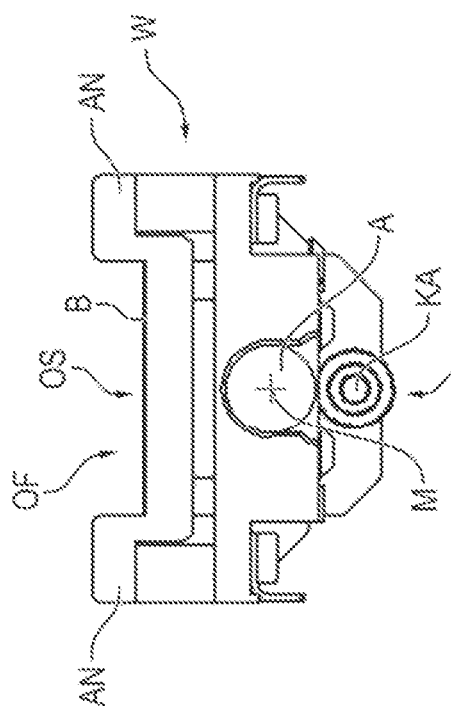
Figure 3B:
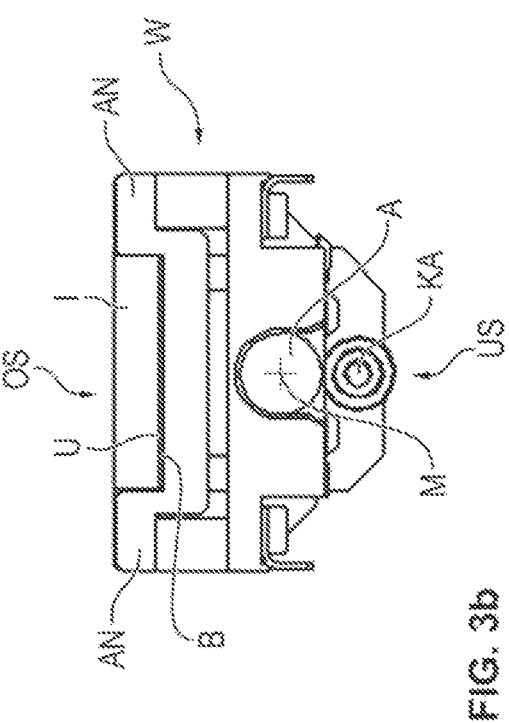

FIG. 3A shows a rocking platform W in a side view without an incubation tray placed in it. FIG. 3B shows a rocking platform W in a side view with an incubation tray I placed in it. The rocking platform W is mounted tiltably about an axis A with a midpoint M. Placed in a reception device AN of the rocking platform W in FIG. 3B is an incubation tray I, which comprises a lower side U that bears on a bottom B of an opening OF of the reception device AN. The upper side OS of the rocking platform and its lower side US are also represented. By means of a force reception element KA, the rocking platform W can be tilted about its axis A. The axis A is in particular a longitudinal axis, which extends along the larger extent direction of the rocking platform. A transverse tilting of the rocking platform may be carried out about the axis A.

FIG. 3C shows once more the rocking platform W, with the incubation tray I placed in it, in a side view obliquely from above. The incubation tray I is placed in the reception device AN. Furthermore represented is an engagement recess EM, which will be discussed in more detail below. FIG. 3D shows once more the rocking platform W, without the incubation tray, in a side view obliquely from above.

FIG. 4A shows the rocking platform W, together with a rocking slider WS, which may be part of a drive unit AE. The rocking slider WS can execute a drive movement in a lateral plane, represented as the direction or plane R, in order by means of a coupling unit K, which may consist of a plurality of component parts, to act on the force reception element KA in order to induce a rocking movement of the rocking platform W. The drive unit therefore preferably generates a lateral movement as the drive movement. The lateral movement of the drive unit AE is converted by means of the coupling mechanism K into a rocking movement of the rocking platform W. The force reception element KA is arranged eccentrically with respect to the axis A of the rocking platform W, so that a deflection of the force reception element KA about the axial midpoint of the axis A causes tilting of the rocking platform.

The coupling mechanism K consists in this exemplary embodiment of at least one pusher element MI, the force reception element KA and at least one spring element F. The force reception element KA on the rocking platform W may be regarded as part of the coupling mechanism K. If the force reception element KA is deflected by force transmission of a force from one of the pusher elements MI in the direction or the plane R, a rocking movement of the rocking platform W takes place, as represented in FIGS. 4B and 4C for the specific directions R1 and R2, respectively. In the neutral position, the incubation tray in the rocking platform is in a flat position relative to the surface of the Earth.

In other words, the coupling mechanism K comprises at least one pusher element MI, which, because of the drive movement of the drive unit AE, induces a force on the force reception element KA in order to deflect the force reception element, a force transmission from the pusher element MI to the force reception element KA being coupled to the spring element F.

The pusher elements MI are mounted rotatably at so-called rotation points DP. The spring element F is configured in such a way that, in the absence of restraint of the rocking platform W, the drive movement of the drive unit AE, or of the rocking slider WS, causes the rocking movement of the rocking platform W through the angle range. If no restraint of the rocking platform is carried out by a holding force, the spring element F is essentially not deformed during the conduct or continuation of the drive movement for causing the rocking movement. The effect achieved in this way is that a drive coupling between the drive unit AE, or the rocking slider WS, and the rocking platform W is configured in such a way that there is no perceptible mechanical play between the drive unit AE and the rocking platform W. Otherwise, in the case of significant mechanical play, undesired oscillations or undesired movements of the rocking platform W could take place. Such undesired movements so could interfere with controlled flow of the liquid in the incubation tray.

FIG. 5 shows a preferred embodiment of a drive unit AE, in which a motor MO, preferably a stepper motor, is coupled to at least one rocking slider WS as part of the drive unit AE. Preferably, a plurality of rocking sliders WS are coupled to the motor MO, in particular by means of a linkage GS. The motor thus subjects the rocking sliders WS to the drive movement in the plane or direction R. In this way, a plurality of rocking platforms W are thus then subjected to the corresponding rocking movements. The individual axes of the individual rocking platforms W may preferably also be configured as common rotation axes when a plurality of rocking platforms are arranged in succession, as represented in FIG. 2.

FIG. 6 shows a preferred embodiment of a rocking slider WS for tilting or rocking a plurality of rocking platforms next to one another.

FIG. 7A shows an approach of a holding device H to a rocking platform.

FIG. 7B shows the way in which the holding device H restrains one individual rocking platform W while the other rocking platforms continue to be subjected to the rocking movement because of the drive movement.

FIG. 8A shows once more in a side view the holding device H which is restraining the rocking platform W so that the rocking platform W can no longer rotate about the axis A. Details in this regard are represented, in particular, in detail Z. Although the rocking slider WS is still carrying out the drive movement in the direction R1, the pusher MI on the left-hand side is no longer causing any deflection or tilting of the rocking platform despite bearing on the force reception element KA. This is achieved in that the coupling mechanism K causes coupling between the rocking platform W and the drive unit AE, or the rocking slider WS, in an elastically resilient way such that, when the rocking platform W is restrained, the rocking platform W can remain in a fixed position despite continuation of the drive movement.

The spring element F is configured in such a way that, when a holding force is applied in order to restrain the rocking platform, particularly in the neutral position, and at the same time the drive movement is continued, it is deformed merely elastically but not plastically. In the case in which no holding force is applied in order to restrain the rocking platform, the spring element F is essentially not deformed when the drive movement for causing the rocking movement is continued. This thus makes it possible to restrain the rocking platform, preferably by a holding device H, in order then to place an incubation tray in the rocking platform W or take it out. It is furthermore possible to carry out aspiration of liquid in the incubation tray, or else to pipette liquid into the incubation tray, during the restraint. The dynamic properties of the rocking movement of the rocking platform W for further operation or use are, however, not affected by the restraint of the rocking platform W, since the spring element F is configured in the manner as mentioned above so that the mechanical properties of the mechanical coupling between the drive unit and the rocking platform are not modified by the restraint of the rocking platform. The restraint may be regarded as stopping the rocking movement without modifying the mechanical properties of the coupling unit for tilting the rocking platform for subsequent operation.

FIG. 8B shows the effect, similar to that which was described in FIG. 8A, for the case in which the movement of the rocking slider WS takes place in the direction R2 opposite to the direction R1 of FIG. 8a. A deflection of the pusher element MI on the right-hand side takes place because of the elastic spring F. Details are in this case shown in the detail Y.

By the incubation device according to the invention, it is possible to restrain the rocking platform in any position within the angle range, without interfering with the properties of the mechanical coupling between the drive unit and the rocking platform for subsequent operation, or for subsequent instants, since the coupling mechanism is configured elastically resiliently.

Not only may the restraint of the rocking platform be carried out in the manner as shown in FIG. 8A or FIG. 8B, but it may also be carried out in a so-called oblique position of the rocking platform in order to force a flow of liquid inside the incubation tray to one of the sides in the incubation tray. The restraint of the rocking platform is in particular a restraint against the rocking movement. In particular, this may be carried out by applying a holding force from the outside. The rocking platform remains in a fixed position during the restraint of the rocking platform despite the drive movement of the drive unit continuing to be carried out.

FIG. 9A shows a preferred embodiment of a holding device, which comprises on its lower side an engagement element EE that has an essentially convex geometrical shape KOF. The holding device H furthermore comprises a gripping element GR which can be moved toward the sides in order to grip an incubation tray during a transport process or, alternatively, to remove or pick out an incubation tray from a rocking platform. By means of the holding device H, an incubation tray can thus be transported to a rocking platform, preferably by using the gripping elements GR. Furthermore, the incubation tray may be placed in a rocking platform after retraction of the gripping elements GR toward the sides.

FIG. 9B shows once more the holding device from a further perspective, in which a chamfer SCR of the engagement element EE is also made clear, or visible. The engagement element EE can then engage in an engagement recess EM, as shown in FIG. 3B, when the holding device H approaches a rocking platform W. The engagement recess EM then has an essentially concave geometrical shape, which corresponds to the convex geometrical shape of the engagement element EE.

FIGS. 10A to 10D show the holding device H in different positions relative to a rocking platform W, which is at least partially still carrying out a rocking movement because of a drive movement of the drive unit. The rocking platform W performs the rocking movement in an XZ plane, as can be seen from FIG. 10A, the rotation axis about which the rocking platform W is tilted, or acts, extending in the Y plane, perpendicular to the image plane of the representation. The holding device H approaches the upper side of the rocking platform in the Z direction. In this case, the engagement element EE engages in the engagement recess EM, represented by dashes in FIGS. 10C and 10D. By the dashed representation of the engagement recess EM in FIGS. 10C and 10D while comparing with the representation of the upper opening of the engagement recess EM of FIG. 3B, the way in which the engagement recess EM is to be configured becomes clear to the person skilled in the art. The engagement of the engagement element EE in the engagement recess EM prevents the rocking movement of the rocking platform W in the fixed position, as shown in FIG. 10D.

As can be seen from FIGS. 9A and 9B, the engagement element EE is rounded on its outer sides ST. The effect of this is that when the holding device H approaches the rocking platform W, irrespective of an actual position of the rocking platform W, the engagement element EE can also engage in an edge region RB of the reception device AN, in its opening OF, without leading to mechanical arresting or mechanical locking in one of the intermediate states of FIG. 10B or 10C during the approach of the holding device H to the rocking platform W.

FIG. 11A shows a holding device H with a rocking platform W in a further embodiment, an incubation tray I being placed in the rocking platform W. Below the rocking platform W, there is a metal element, fastened on the rocking platform W, on the lower side of the rocking platform.

FIG. 11B shows an opening OF, located on an upper side of the rocking platform W, of the reception device AN. As mentioned above with reference to FIG. 3A. the reception device AN comprises a bottom B on which a lower side U of the incubation tray bears in the inserted state.

Preferably, the rocking platform comprises a heating device HZ for heating an incubation tray I.

The reception device AN furthermore comprises a clamping mechanism, which in this embodiment is provided by two clamping mechanism elements KL1, KL2. The clamping mechanism KL1, KL2 causes holding of the lower side of the incubation tray I on the bottom B of the rocking platform W. In this way, firm mechanical fixing or holding of an incubation tray on the rocking platform is thus achieved, so that the incubation tray I is mounted reliably in the rocking platform W while a rocking movement is being carried out.

That part of the clamping mechanism KL1 which is shown in more detail in the detail X is movable in such a way that it can be moved outward in a direction R11, so that a projection of the incubation tray I is then exposed. A part GR of the gripping element can also be seen in the detail X.

The clamping mechanism element KL1 can also be moved back again counter to the direction R11, preferably by a spring force. This is represented in FIG. 11C in the detail Z. The clamping mechanism element KL1 thus restrains the incubation tray I in this region, as represented as detail Z in FIG. 11C.

A clamping mechanism element KL2, which comprises a hollow AN, is furthermore represented in the detail W of FIG. 11B. When the incubation tray I is moved in the direction R12, engagement of the incubation tray I in a hollow AN of the clamping mechanism element KL2 is induced, as also represented in FIG. 11C in detail Y.

The clamping mechanism KL1, KL2 not only causes firm fixing of the incubation tray I on the rocking platform W in order to restrain the incubation tray I while the rocking movement is being carried out by the rocking platform W. By holding the lower side of the incubation tray on the bottom of the opening of the reception device, the clamping mechanism KL1, KL2 may also cause a thermal junction or a thermal contacting between the heating device HZ of the rocking platform W and the incubation tray I to be maximized or ensured. Heating of liquid may be necessary in the course of pathohistochemical processing of a sample. In the course of heating, bending of the incubation tray I may take place, so that it no longer bears surface-wide with its lower side U on the bottom B, but becomes curved so that the thermal junction or the thermal contacting is reduced. Because the clamping mechanism KL1, KL2 restrains the lower side U of the bottom of the incubation tray I on the bottom B, the thermal junction or the thermal contacting is improved.

FIG. 12A shows in detail a metal element MT, which is mechanically firmly coupled to the rocking platform W and carries out the rocking movement with the rocking platform. Furthermore shown is an electromagnet ELM, which can preferably be driven, or activated and deactivated, by means of a schematically represented control unit SE. The control unit is furthermore configured to drive the holding device, as illustrated schematically in FIG. 12A.

The control unit SE is configured so that the holding device H is driven in such a way that it restrains the rocking platform in the fixed position, preferably by means of engagement of the engagement element in the engagement recess. The control unit is furthermore configured subsequently to activate the electromagnet so that a magnetic force between the electromagnet and the metal element restrains the rocking platform in the fixed position even when the holding device of the rocking platform is no longer restraining. The effect achieved by this is that the rocking platform W can initially be brought into a fixed position by a holding device H, which may then however at the subsequent instant be done merely by the electromagnet ELM, so that the holding device H can be removed again from the rocking platform W. In this way, a pipetting unit may then thus be brought up to the incubation tray at a subsequent instant, without the holding device H still having to restrain the rocking platform W, so that more space is thus available for pipetting in the region of the incubation tray.

FIG. 13A shows a preferred unit of a washing unit WA, which can aspirate liquid on the incubation tray by means of individual aspiration devices DS, preferably nozzles or aspiration nozzles DS. Preferably, the wash unit WA comprises its own engagement unit EE. By means of individual needles NA, liquid can then be brought to an incubation tray via a connecting unit AS by means of pipetting.

FIG. 13B shows the wash unit WA in a front view.

The invention claimed is:
1. An incubation device, comprising:
a multiplicity of rocking platforms, which are respectively mounted tiltably about a respective axis, the respective rocking platform comprising a respective reception device for mechanically reversible reception of a respective incubation tray, a common drive unit for common generation of respective rocking movements of the respective rocking platforms through a particular angle range on the basis of a drive movement of the drive unit, wherein each of the respective rocking platforms is coupled to the common drive unit by a respective coupling mechanism, and wherein each of the respective coupling mechanisms elastically resiliently couples the respective rocking platform to the common drive unit in such a way that, when the rocking platform is restrained, the rocking platform remains in a fixed position despite continuation of the drive movement, but furthermore, after the restraint of the rocking platform is ended, the rocking platform again carries out the rocking movement through the particular angle range because of the drive movement, wherein the coupling mechanism comprises at least one elastic spring element, which is configured in such a way that the at least one elastic spring element is elastically deformed in the event of application of a holding force to restrain the rocking platform and simultaneous continuation of the drive movement.

2. The incubation device as claimed in claim 1, wherein the rocking platform comprises a force reception element arranged eccentrically with respect to the axis of the rocking platform, the deflection of which about an axis midpoint causes tilting of the rocking platform, wherein the coupling mechanism further comprises at least one pusher element which, because of the drive movement of the common drive unit, generates a force on the force reception element to deflect the force reception element, and wherein a force transmission from the pusher element to the force reception element is coupled to the at least one elastic spring element.

3. The incubation device as claimed in claim 1, further comprising a holding device for restraining at least one of the rocking platforms in the fixed position.

4. The incubation device as claimed in claim 3, wherein the common drive unit is arranged below the rocking platform, wherein the holding device comprises on its lower side an engagement element having an essentially convex geometrical shape, wherein the rocking platform further comprises on its upper side an engagement recess having an essentially concave geometrical shape, which corresponds with the convex geometrical shape of the engagement element, and wherein movement of the holding device from above in a direction of the upper side of the rocking platform causes engagement of the engagement element in the engagement recess in order to prevent the rocking movement of the rocking platform in the fixed position.

5. The incubation device as claimed in claim 1, wherein the rocking platform further comprises a metal element, which is firmly mechanically coupled to the rocking platform and carries out the rocking movement together with the rocking platform, wherein the incubation device further comprises an electromagnet and a control unit, wherein the control unit is configured to drive the holding device in such a way that the holding device restrains the rocking platform in the fixed position, and furthermore subsequently to activate the electromagnet so that a magnetic force between the electromagnet and the metal element also restrains the rocking platform in the fixed position when the holding device no longer restrains the rocking platform.

6. The incubation device as claimed in claim 5, wherein the holding device restrains the rocking platform in the fixed position by engaging the engagement element in the engagement recess.

7. The incubation device as claimed in claim 1, wherein the reception device is configured with an upwardly open opening on an upper side of the rocking platform, into which the incubation tray can be inserted.

8. The incubation device as claimed in claim 7, wherein the reception device comprises a bottom on which a lower side of the incubation tray bears in an inserted state, and wherein the reception device further comprises a clamping mechanism in order to hold the lower side of the incubation tray on the bottom.

9. The incubation device as claimed in claim 8, wherein the rocking platform further comprises a heating device for heating the bottom.

10. A system, comprising:

the incubation device as claimed in claim 1 and at least one of the incubation tray which can be placed in the rocking platform.

11. The system as claimed in claim 10, wherein the incubation tray comprises an indentation, formed by walls of the incubation tray, having an indentation bottom, wherein the incubation tray comprises at least one opening which opens into a channel at a longitudinal end of the indentation, so that liquid can be introduced into the indentation, or aspirated, through the channel, wherein a carrier may be placed in the incubation tray, which carrier comprises a sample on its lower side, which faces toward the indentation bottom, when it is placed in the incubation tray, so that the lower side of the carrier, the indentation bottom and the walls form a compartment for the liquid.

12. The system as claimed in claim 11, wherein the incubation tray comprises means for fixing a distance between the lower side of the carrier and the indentation bottom such that the lower side of the carrier, the indentation bottom and the walls form the compartment for the liquid.

13. The system as claimed in claim 12, wherein the means for fixing a distance between the lower side of the carrier and the indentation bottom comprise a bearing chamfer.

14. The system as claimed in claim 11, wherein the at least one opening is placed in the walls of the incubation tray.

* * * * *